(12) United States Patent
Luo

(10) Patent No.: US 12,741,113 B2
(45) Date of Patent: Sep. 22, 2026

(54) HEADGEAR FOR USE IN THE PAP FIELD

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/416,287

(22) Filed: Jan. 18, 2024

(65) Prior Publication Data

US 2025/0235655 A1 Jul. 24, 2025

(51) Int. Cl.
*A61M 16/06* (2006.01)

(52) U.S. Cl.
CPC ............................... *A61M 16/0683* (2013.01)

(58) Field of Classification Search
CPC ................................................. A61M 16/0683
See application file for complete search history.

(56) References Cited

U.S. PATENT DOCUMENTS 5,724,677 A * 3/1998 Bryant ............... A41D 13/1146 2/206
6,070,579 A * 6/2000 Bryant ............... A41D 13/1161 128/207.11
6,148,817 A * 11/2000 Bryant ................... A61B 50/30 128/207.11
10,653,901 B2 * 5/2020 Nguyen ............. A41D 13/1161
2019/0351172 A1 * 11/2019 Formica .................... B32B 5/18
2020/0109847 A1 * 4/2020 Poggio ................... A61B 90/35
2020/0306481 A1 * 10/2020 Kooij ................ A61M 16/0683
2021/0016041 A1 * 1/2021 Huddart ............ A61M 16/0683
2022/0370749 A1 * 11/2022 Dunn .................. B29C 66/4322
2023/0086237 A1 * 3/2023 Bearne .............. A61M 16/0622 128/206.24
2023/0149651 A1 * 5/2023 Scheiner ........... A61M 16/0672 128/206.24
2023/0181859 A1 * 6/2023 Hammer ........... A61M 16/0688 128/206.25
2023/0211107 A1 * 7/2023 Kooij ................ A61M 16/0633 128/206.24
2024/0173505 A1 * 5/2024 Scheiner ............... A61M 16/10

* cited by examiner

*Primary Examiner* — LaToya M Louis
(74) *Attorney, Agent, or Firm* — Birch, Stewart, Kolasch & Birch, LLP

(57) ABSTRACT

A headgear for use in the Positive Airway Pressure field includes an inner layer, a bonding layer, a padding layer, film layers, and an adhesive. The inner layer is configured to be at least partially in contact with a patient's skin during use, while the bonding layer is configured to adhere an outer side of the headgear, which comes into contact with the air, to a fixed part by folding the headgear, thereby tightening or loosening the headgear. The padding layer, placed between the inner layer and the bonding layer, increases thickness. The film layers are provided between the inner layer and the padding layer, as well as between the padding layer and the bonding layer. The adhesive is configured to bond the layers together. The headgear has at least three layers and is made of at least two types of textile materials.

24 Claims, 21 Drawing Sheets

HEADGEAR FOR USE IN THE PAP FIELD

TECHNICAL FIELD

This disclosure pertains to a headgear for use in the Positive Airway Pressure (PAP) field, to be used in conjunction with patient interface assemblies. It includes an inner layer, a bonding layer, a padding layer, film layers, and an adhesive. The headgear is applicable for one or more of the treatments and improvements of respiratory diseases.

BACKGROUND

Sleep Apnea Syndrome (SAS) is a sleep disorder characterized by pauses in breathing or shallow breathing during sleep. The pauses can last from a few seconds to several minutes and may occur multiple times throughout the night. Commonly, sleep apnea results in loud snoring and may be accompanied by choking or snorting sounds when the patient resumes breathing. Severe cases can lead to symptoms like excessive daytime sleepiness or extreme fatigue. In children, sleep apnea can contribute to various behavioral problems at school, such as attention deficit and symptoms of hyperactivity, particularly Attention Deficit and Hyperactivity Disorder (ADHD). Currently, there are three distinct types of sleep apnea: Obstructive Sleep Apnea (OSA), Central Sleep Apnea (CSA) caused by central nervous system disorders, and Mixed Sleep Apnea Syndrome (MSAS), which combines symptoms of both, with OSA being the most commonly occurring symptom. Studies indicate that approximately 34% of middle-aged men and 17% of middle-aged women meet the diagnostic criteria for OSA. This prevalence rises to 40%-80% among patients with cardiovascular diseases like hypertension, heart failure, coronary artery disease, pulmonary arterial hypertension, atrial fibrillation, and cerebral stroke. Symptoms of OSA include snoring, breathing difficulties, fragmented sleep, and daytime sleepiness. Risk factors involve obesity, a thick neck, craniofacial abnormalities, smoking, family history, and nighttime nasal congestion. Effective treatment for patients diagnosed with OSA, such as lifestyle and behavioral changes, weight loss for overweight patients, should be promptly implemented.

For patients with moderate to severe OSA, especially those whose sleep quality and health are severely impacted by frequent breathing pauses, timely PAP therapy should be given. PAP treatment involves a specialized ventilator delivering continuous positive pressure airflow to the patient's upper airways, including the larynx and nasal passages, to prevent collapse or blockage of the airways, thereby avoiding apnea episodes. Patients typically wear a patient interface cushion (a face mask or a nasal mask) connected to the PAP machine to receive the airflow. A headgear is required to secure the patient interface cushion to the patient's face, whose main function is to secure the patient interface cushion that is connected to a PAP machine to the face, ensuring that the machine remains in place throughout the night without falling off or loosening and causing air leakage. Besides, since part of the headgear contacts the skin, the headgear is generally made from soft, skin-friendly materials like sponges and textiles. And the headgear often includes adjustable parts, allowing patients to adjust the headgear's tightness according to their comfort level and the seal of the mask, ensuring proper safety and airtightness. However, the frequent fastening and unfastening, typically using elements like hook-and-loop fasteners, can cause the already difficult adherence between the sponge and textile materials to loosen, leading to faster wear and tear of the headgear. This issue is one of the main reasons why sponge-based PAP headgears are prone to damage, making the improvement of their comfort and durability an important aspect to address in the current market.

The headgears available on the market are mostly made by wrapping a layer of sponge between the inner layer and the outer layer of textile material. This design presents several limitations and contributes to increased production costs and higher damage rates. The different material properties of the sponge and fabric make it difficult for them to adhere together, necessitating edging or overlocking to prevent fraying and delamination. Additionally, the presence of the sponge layer makes the textile material prone to curling at the edges. The bond between sponge and textile is not as strong as that between textile materials. Using textile materials alone for headgears is more comfortable, and softer headgears are a better choice for patients. Cleaning headgears made from a combination of sponge and textile presents challenges for patients, including issues with slow drying and easy delamination.

SUMMARY

Therefore, introducing a more comfortable and durable headgear is an essential task that offers benefits to both patients and producers. The headgear provided in this disclosure, made from mutually adhering textile materials, addresses multiple issues present in current market offerings and offers better wearing comfort, breathability, flexibility, and ease of cleaning, making it a more competitive product in the market. This design better helps patients accept PAP therapy, ensuring treatment continuity and improving patient compliance with the treatment.

The objective of this disclosure is to provide a new type of headgear for use in the PAP field that offers improved durability, easier manufacturing, quicker market adaptability, more comfortable and safer use, and overcomes the limitations of existing similar technologies. In this way, the headgear provided in this disclosure is more effective, applicable in a broader range of scenarios, along with more accessible methods, stably securing the patient interface cushion on the patient's face and coordinating with other components to treat sleep breathing disorders.

A headgear for use in a PAP field is provided in this disclosure, configured to secure a patient interface cushion to the face of a patient and to work in conjunction with other components to treat sleep apnea, the headgear including at least some of the following elements or features.

An inner layer is configured to be at least partially in contact with a skin of the patient during use and the inner layer has at least one of the following features: 1) a Grams per Square Meter value of at or between 100 to 450 g/m$^2$; 2) material containing 5% to 50% spandex; and 3) a thickness of less than 3 mm.

A bonding layer, with a greater roughness than the inner layer, is different in the composition or quantity of composition from the inner layer. The bonding layer is configured to adhere an outer side of the headgear that comes into contact with air to a fixed part by folding the headgear to tighten or loosen the headgear.

A padding layer is configured to be placed between the inner layer and the bonding layer to increase thickness.

An adhesive is configured to bond the layers together.

And the inner layer, the bonding layer, and the padding layer are all textile materials.

In one embodiment, the padding layer is a combination of multiple layers of textile materials.

In one embodiment, the headgear has a certain degree of elasticity in all directions, and the elasticity is maximum along a lengthwise direction of the headgear.

In one embodiment, a material of the adhesive includes a combination of one or more of thermoplastic polyurethane, polyurethane reactive adhesives, or other ordinary adhesives.

In one embodiment, the inner layer, the bonding layer, and the padding layer of the headgear are of equal size and their outer edges are aligned with each other.

In another embodiment, a headgear for use in a PAP field is provided, configured to secure a patient interface cushion to the face of a patient and to work in conjunction with other components to treat sleep apnea, the headgear including at least some of the following elements or features.

An inner layer is configured to be at least partially in contact with the skin of the patient during use.

A bonding layer, different in the composition or quantity of composition from the inner layer and more readily adhesive to a fixed part, is configured to adhere an outer side of the headgear that comes into contact with air to the fixed part by folding the headgear to tighten or loosen the headgear.

The bonding layer has at least one of the following features: 1) including a blend of nylon and spandex; 2) a Grams per Square Meter value of at or between 100 to 450 g/m$^2$; and 3) a thickness of no less than 0.3 mm.

A padding layer is configured to be placed between the inner layer and the bonding layer to increase thickness.

An adhesive is configured to bond the layers together.

The inner layer, the bonding layer, and the padding layer are all textile materials, and the headgear includes at least two types of textile materials.

In one embodiment, the padding layer is a combination of multiple layers of textile materials.

In one embodiment, the inner layer has greater stretchability than the bonding layer.

In one embodiment, a material of the adhesive includes a combination of one or more of thermoplastic polyurethane, polyurethane reactive adhesives, or other ordinary adhesives.

In one embodiment, the bonding layer is rougher than the inner layer.

In yet another embodiment, a headgear for use in a PAP field is provided, configured to secure a patient interface cushion to a face of a patient and to work in conjunction with other components to treat sleep apnea, the headgear including at least some of the following elements or features.

An inner layer is configured to be at least partially in contact with a skin of the patient during use.

A bonding layer, with a greater roughness than the inner layer, is different in the composition or quantity of composition. The bonding layer is configured to adhere an outer side of the headgear that comes into contact with air to the fixed part by folding the headgear to tighten or loosen the headgear.

A padding layer is configured to be placed between the inner layer and the bonding layer to increase thickness.

The film layers are provided between the inner layer and the padding layer, as well as between the padding layer and the bonding layer.

An adhesive is configured to bond the layers together.

The headgear has five layers and includes at least two types of textile materials.

In one embodiment, the padding layer is a single-layer material including foam material or textile material.

In one embodiment, apart from the adhesive and the film layers, the headgear is made of textile materials.

In one embodiment, a thickness of the padding layer is less than the thickness of the inner layer.

In one embodiment, a material of the film layers is thermoplastic polyurethane.

In another embodiment, a headgear for use in a PAP field is provided, configured to secure a patient interface cushion to a face of a patient and to work in conjunction with other components to treat sleep apnea, the headgear including at least some of the following elements or features.

An inner layer is configured to be at least partially in contact with a skin of the patient during use. And the inner layer has at least one of the following features: 1) a Grams per Square Meter value of at or between 100 to 450 g/m$^2$; 2) material containing 5% to 50% spandex; and 3) a thickness of less than 3 mm.

A bonding layer, with a greater roughness than the inner layer, is different in the composition or quantity of composition from the inner layer. The bonding layer is configured to adhere an outer side of the headgear that comes into contact with air to the fixed part by folding the headgear to tighten or loosen the headgear.

A padding layer is configured to be a single-layer material or a multi-layer material placed between the inner layer and the bonding layer to increase thickness.

An adhesive is configured to bond the layers together.

The headgear comprises at least three layers, with the inner layer, the bonding layer, and the padding layer all being textile materials.

In one embodiment, a material of the adhesive includes a combination of one or more of thermoplastic polyurethane, polyurethane reactive adhesives, or other ordinary adhesives.

In one embodiment, the padding layer is a single-layer material, with a composition and quantity of composition different from other layers.

In one embodiment, the padding layer includes multiple layers, and a thickness of the padding layer is greater than the thickness of the inner layer and the bonding layer.

In one embodiment, the bonding layer and the fixed part are bonded together by thermal pressing.

In yet another embodiment, a headgear for use in a PAP field is provided, configured to secure a patient interface cushion to a face of a patient and to work in conjunction with other components to treat sleep apnea, the headgear including at least some of the following elements or features.

An inner layer is configured to be at least partially in contact with a skin of the patient during use. And the inner layer has at least one of the following features: 1) a Grams per Square Meter value of at or between 100 to 450 g/m$^2$; 2) material containing 5% to 50% spandex; and 3) a thickness of less than 3 mm.

A bonding layer, different in the composition or quantity of composition from the inner layer, is configured to adhere an outer side of the headgear that comes into contact with air to the fixed part by folding the headgear to tighten or loosen the headgear. The bonding layer has at least one of the following features: 1) including a blend of nylon and spandex; 2) a Grams per Square Meter value of at or between 100 to 450 g/m$^2$; and 3) a thickness of no less than 0.3 mm.

A padding layer is configured to be a single-layer material or a multi-layer material placed between the inner layer and the bonding layer to increase thickness.

An adhesive is configured to bond the layers together.

And the headgear comprises at least three layers and includes at least two types of textile materials.

In one embodiment, a material of the adhesive includes a combination of one or more of thermoplastic polyurethane, polyurethane reactive adhesives, or other ordinary adhesives.

In one embodiment, the inner layer has greater stretchability than the bonding layer.

In one embodiment, the headgear has a certain degree of elasticity in all directions, and the elasticity is maximum along a lengthwise direction of the headgear.

In one embodiment, the padding layer is foam material or textile material, and the padding layer includes multiple layers.

The benefits of a headgear provided by this disclosure can at least include:

1) The headgear is more durable and less likely to get damaged with subsequent use, saving patients the cost of repurchasing. Durability is one of the key concerns for patients, especially those with OSA who need to repeatedly put on and adjust the headgear multiple times every night to achieve the right tightness and comfort for their head. This places higher demands on the headgear's durability. a) Headgears currently available on the market often have a sponge layer beneath the bonding layer. However, due to the different material properties of the sponge and textile, they are prone to separation. Additionally, some market headgears with the sponge layer that do not have edging or overlocking tend to fray and delaminate over time. Frequent attaching and detaching of the bonding layer from the fixed part can separate the bonding layer from the sponge, damaging the headgear. Moreover, constant pulling between the bonding layer and the fixed part can also damage the bonding layer itself, rendering it ineffective. The headgear provided in this disclosure does not include a sponge layer. The similar characteristics of the textile materials make bonding between textile materials easier compared to the bonding between sponge and textile. Thus, under the same frequency of attaching and detaching from the fixed part, the headgear made solely of textile materials in this disclosure is more durable than those made of textile and sponge, allowing for longer use by patients with OSA. b) The headgears are generally long-strip in shape and typically exceed 10 cm in length. Long-strip sponge materials, usually made of soft foam or sponge-like polymers, are more susceptible to external forces due to their softness, as opposed to textile materials which are less likely to undergo irreversible shape changes. As a result, textile materials can maintain a relatively flat shape and are less susceptible to curling under external pressure, whereas sponge materials are more prone to bending or curling due to external deformation. Besides, the high deformability of sponge materials means they are more likely to change the shape when subjected to external forces, increasing the risk of curling. Environmental factors such as temperature, humidity, and air pressure can also alter the shape of the sponge, whereas textile materials are more stable. In summary, a headgear formed from the joining of textile materials is less likely to suffer various types of damage and can withstand frequent adjustments (attaching and detaching from the fixed part) without losing performance or structural integrity. Its resistance to damage means that even with frequent fine-tuning by patients, the headgear will maintain its original performance. As the headgear provided in this disclosure has a longer lifespan, patients do not need to purchase replacements frequently, thereby reducing their repurchase costs. As such, the headgear of this disclosure is an economically viable choice for patients and helps to lower the overall cost of treatment.

2) The headgear in this disclosure is relatively simple to manufacture and has lower costs, as well as having fewer processes, which enables rapid market adaptability. The headgears currently available on the market often incorporate a sponge layer sandwiched between textile materials. Due to the difficulty in bonding sponge to textile and the ease of separation under external force, the headgears typically require the sponge to be encased within textile materials and then edge-bonded or overlocked using techniques like thermal pressing or ultrasonic. In contrast, the headgear provided by this disclosure joins textile materials to each other. Since all layers are made of textile materials, they bond more effectively, eliminating the need for edging or overlocking, and ensuring easy adhesion without easy separation. While the existing market process for headgears involves material cutting, compounding, physical overlocking, and stitching, the process for this disclosure is simplified to cutting and stitching, reducing the overlocking step and thereby lowering production costs. This reduction includes savings in labor, equipment, raw materials, and energy, enhancing production efficiency through cost savings. Improved production efficiency means products can be brought to market more quickly and adapt faster to market changes. Moreover, each production step carries a certain risk of errors and defects; reducing the number of steps decreases the likelihood of product defects, thus enhancing quality and reliability.

3) The headgear provided by this disclosure utilizes a film layer of thermoplastic polyurethane and polyurethane reactive adhesives to connect the material layers. This approach is safer and more environmentally friendly compared to existing headgears, which are typically bonded using ordinary adhesives. Additionally, the enhanced durability of the headgear results in a reduced discard rate, further reflecting a green and eco-friendly design. Thermoplastic polyurethane is usually non-volatile and does not release harmful volatile organic compounds, ensuring that its use in bonding does not adversely affect the air quality, thereby contributing to a healthier environment. When it comes to recycling the headgear, thermoplastic polyurethane can be easily separated from other materials for recycling purposes. Some thermoplastic polyurethane materials are biodegradable, which means that they can break down into harmless substances under specific conditions. Certain thermoplastic polyurethane materials can even be recycled for the manufacturing of new products. Polyurethane reactive adhesives, known for their rapid hardening, possess strong adhesive strength and high temperature resistance, outperforming ordinary adhesives in speed of production and durability. And polyurethane reactive adhesives typically exhibit good water resistance, which are suitable for use in humid environments without being susceptible to moisture absorption or detachment. The bonding surface with polyurethane reactive adhesives is very smooth, making the adhesive connection between materials imperceptible to the patient, thus enhancing comfort while also improving the aesthetic appeal of the product. In contrast, ordinary adhesives often contain harmful organic solvents and chemicals, which can pose environmental issues during use and disposal. Using thermoplastic polyurethane and polyurethane reactive adhesives instead of ordinary adhesives is a step towards sustainable development and climate change mitigation and represents an environmentally friendly green design approach. The disclosure aligns with the goal of green design, and due to the durability of the headgear, patients do not need to replace the headgear frequently, thereby reducing the number of discarded products and contributing to a lesser environmental impact, thereby achieving long-term green design goals.

4) Compared to existing headgears on the market, the headgear provided by this disclosure features a more skin-friendly inner layer, a better adhering bonding layer, and the use of anti-static textile materials, all of which contribute to improved quality and comfort. The textile materials used in the skin-contacting inner layer of the headgear in this disclosure are more skin-friendly and softer than those used in the headgears available on the current market. This reduces potential friction and irritation to the skin, lowers the risk of allergic reactions and discomfort for the patient, and helps maintain the skin health of patients. Patients generally prefer products made of skin-friendly materials as they provide better comfort and a more pleasant user experience. Such a design can increase patient satisfaction and trust in the product. Additionally, the bonding layer used for self-folding adhesion in the headgear of this disclosure has better adhesiveness compared to existing products on the market. The headgear is more stable and less likely to fall off when used by patients with OSA, and it does not damage or destroy the surface of the bonding layer when being separated from the fixed part. Therefore, the headgear can be used more durably, allowing for repeated adhering and separating without losing its stickiness. Moreover, the entire headgear is made of antimicrobial materials. Colorfastness is an essential requirement for textile materials to meet wearing standards. Through color change tests on the samples and staining tests on undyed lining textile materials, it has been found that the colorfastness of the headgear in this disclosure is of a higher grade. In addition, the headgear can be made of anti-static textile materials, reducing the likelihood of generating static electricity during use. Therefore, the headgear provided by this disclosure outperforms existing products in terms of quality and comfort.

DETAILED DESCRIPTION

Figure 1:
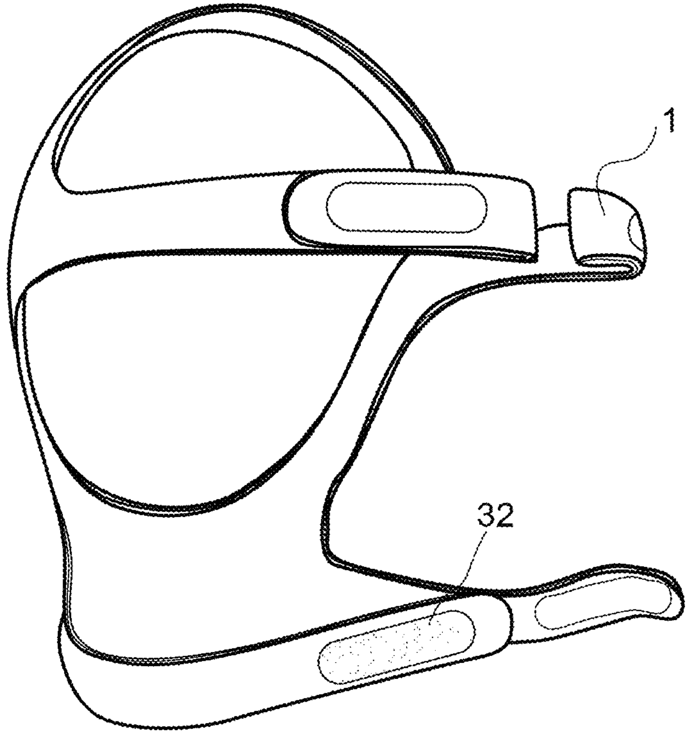
FIG. 1 is a three-dimensional schematic diagram of a form of a headgear in accordance with an embodiment.

To facilitate the understanding of the disclosure, a more comprehensive description will be provided with reference to the relevant drawings. The drawings illustrate typical embodiments of the disclosure. However, the disclosure can be implemented in many different forms and is not limited to the embodiments described herein. On the contrary, the embodiments are provided to make the disclosure more thorough and comprehensive.

Unless otherwise defined, all technical and scientific terms used herein have the same meaning as commonly understood by one of ordinary skill in the art to which this disclosure belongs. The terms used in the specification of the disclosure herein are for the purpose of describing particular embodiments only rather than limiting the disclosure.

This disclosure addresses the issues of susceptibility to damage, discomfort for patients, complex manufacturing processes, and environmental concerns associated with existing headgears in the PAP field, which are configured to secure the patient interface cushion on the patient's face and coordinate with other components. It provides a headgear with a simpler structure and a more comfortable wearing experience for patients. The headgear provided by this disclosure not only addresses the disadvantages of the existing designs but also offers several different structures for patients to choose according to their needs and preferences. The headgear in this disclosure is a better technical innovation for patients, manufacturers, and the market. The choice of safe and environmentally friendly materials for manufacturing also represents a sustainable, eco-friendly design approach.

Detailed embodiments are presented below to elucidate the structures of a headgear for use in the PAP field.

Embodiment 1

This embodiment provides a headgear 1 for use in the PAP field. It includes three-dimensional schematic diagrams, a schematic diagram of how a headgear is worn, a cross-sectional structural schematic diagram, a three-dimensional diagram of the layered structure, and detail displays, as shown in FIGS. 1-8. This embodiment pertains to a headgear 1 for use in the PAP field, primarily involving an inner layer 2, a bonding layer 3, a padding layer 4, film layers 5, and an adhesive 6. The headgear 1 is configured to secure the patient interface cushion on the patient's face, thereby delivering pressurized air from the ventilator into the patient's airway for the treatment of OSA.

The headgear 1 includes an inner layer 2, configured to be at least partially in contact with the patient's skin during use. Due to the skin contact, the material of the inner layer has specific requirements, typically being of a finer texture. Specifically, the inner layer 2 has at least one of the following features: 1) a Grams per Square Meter value of at or between 100 to 450 g/m$^2$; 2) material containing 5% to 50% spandex; and 3) a thickness of less than 3 mm. The percentage share of spandex in the material is derived from an analysis of the composition of the textile material, and the weight of the spandex material is at or between 5% to 50% of the total weight of the textile material. The high content of spandex, a highly elastic fiber that can stretch at or between 6 to 7 times its original length and quickly return to its initial state when the tension is released, lends the inner layer 2 great elasticity. Spandex is also resistant to acids, bases, sweat, seawater, dry cleaning, and wear. Thus, the inner layer 2 is very elastic, configured to stretch along a lengthwise direction of the headgear 1, and has greater stretchability than the bonding layer 3 (when the headgear 1 is stretched along a lengthwise direction, the inner layer 2 deforms more than the bonding layer 3) and the inner layer 2 is made of textile material.

The bonding layer 3, different in the composition or quantity of composition from the inner layer 2, facilitates easier attachment to the fixed part 32. It is configured to adhere the outer side of the headgear 1 that comes into contact with air to a fixed part 32 by folding the headgear 1 to tighten or loosen the headgear 1. The bonding layer 3 has at least one of the following features: 1) including a blend of nylon and spandex; 2) a Grams per Square Meter value of at or between 100 to 450 g/m$^2$; 3) a thickness of no less than 0.3 mm. Specifically, the fixed part 32 connects to different locations of the bonding layer 3 to form spaces of varying circumferences to fit head sizes of different users. The bonding layer 3 and the fixed part 32 are bonded together through thermal pressing. The fixed part 32 can also be connected to the outer side of the bonding layer 3 which contacts the air via ultrasonic joining, sewing, etc. The fixed part 32 has hooks or other structures that tightly connect to the bonding layer 3 during use. The forms of the fixed part 32 include, but are not limited to, hook-and-loop fasteners. The part where the bonding layer 3 connects to the fixed part 32 through self-folding and adhesion is the part prone to damage (as shown in the gray area in FIG. 8). Since the functions and usage characteristics of the bonding layer 3 and the inner layer 2 differ, their compositions or quantities of composition are distinct. The inner layer 2, which contacts human skin, requires a finer material to provide a comfortable user experience. Conversely, the bonding layer 3 requires a rougher surface to connect to the fixed part 32 and typically has an adhesive structure with a surface (like loops), making the bonding layer 3 rougher than the inner layer 2. The roughness of the bonding layer 3 is greater than or equal to 2 μm, and it is made of textile material.

The padding layer 4 is configured to be placed between the inner layer 2 and the bonding layer 3 to increase thickness and enhance comfort during use. The thickness of the padding layer 4 is greater than that of both the inner layer 2 and the bonding layer 3. In this disclosure, the padding layer 4 is made of textile material, which can be a combination of multiple layers of textile material or a single layer of textile material. Since both the inner layer 2 and the bonding layer 3 are made of textile materials and bonding between textile materials is easier, issues like delamination and edge curling can be avoided. Therefore, the headgear 1 provided by this disclosure is more robust and durable compared to existing headgears on the market. The padding layer 4 is different from each of the other layers, and the difference lies in the composition or proportion of composition.

The film layers 5 are placed between the inner layer 2 and the padding layer 4, as well as between the padding layer 4 and the bonding layer 3. The material for the film layers 5 is thermoplastic polyurethane which is usually non-volatile and does not release harmful volatile organic compounds. Therefore, using thermoplastic polyurethane for bonding does not adversely affect the air quality, contributing to a healthier environment. The thickness of the film layers 5 is at or between 0.01 to 0.2 mm, making its impact on the human sensory experience slight and barely noticeable.

The adhesive 6 of the headgear 1 is configured to connect various layers together. The materials for the adhesive include thermoplastic polyurethane, polyurethane reactive adhesives, or other ordinary adhesives (such as epoxy resin, acrylic sealant, etc.). In this embodiment, the adhesive material is polyurethane reactive adhesives, known for their strong bond, shorter curing time, good water resistance, and smoother surface. This disclosure utilizes a combination of the adhesive 6 and the film layers 5 to replace the use of ordinary adhesives found in current products. Ordinary adhesives often contain harmful organic solvents and chemicals, posing environmental issues during use and disposal. Using healthy, green materials represents an environmentally friendly design that positively impacts the environment and carbon neutrality.

Figure 2:
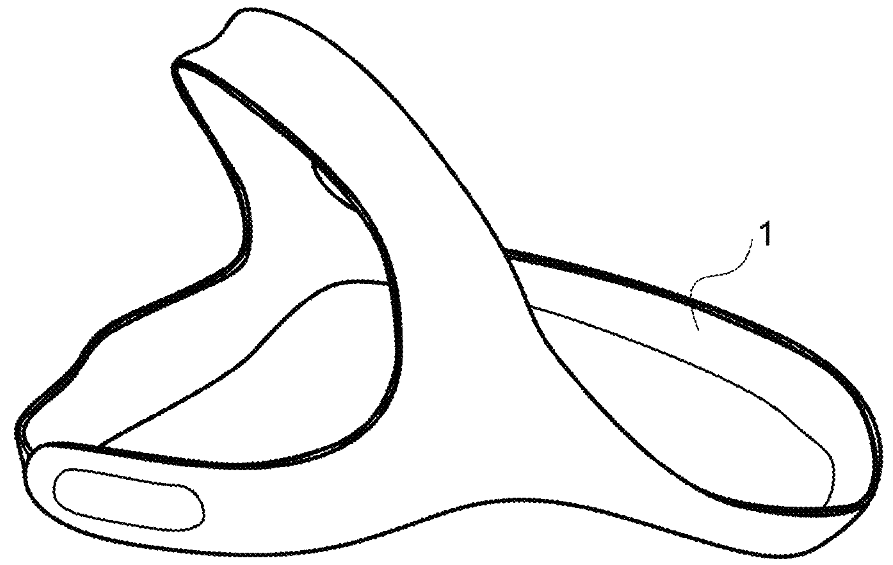
FIG. 2 is a three-dimensional schematic diagram of another form of a headgear in accordance with an embodiment.
Figure 3:
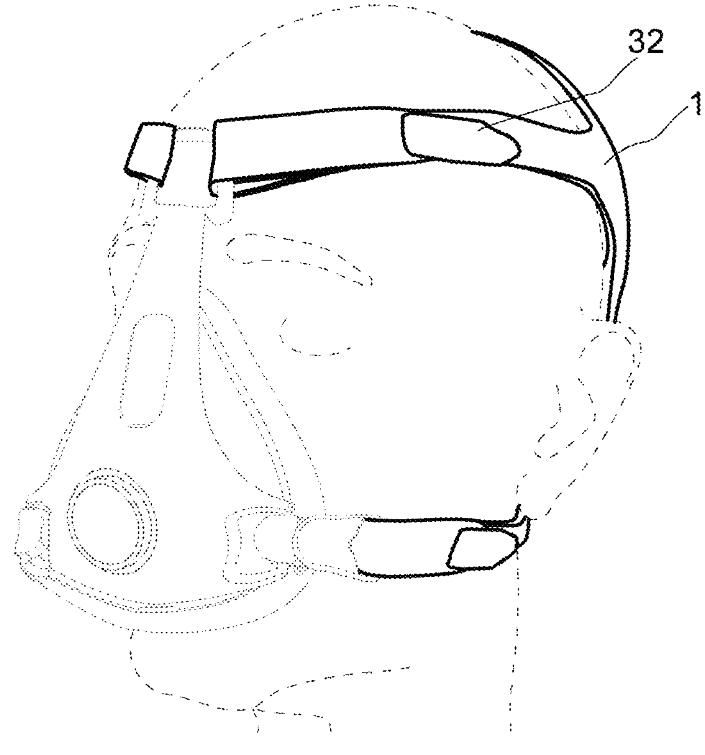
FIG. 3 is a schematic diagram demonstrating how yet another form of a headgear is worn in accordance with an embodiment.
Figure 4:
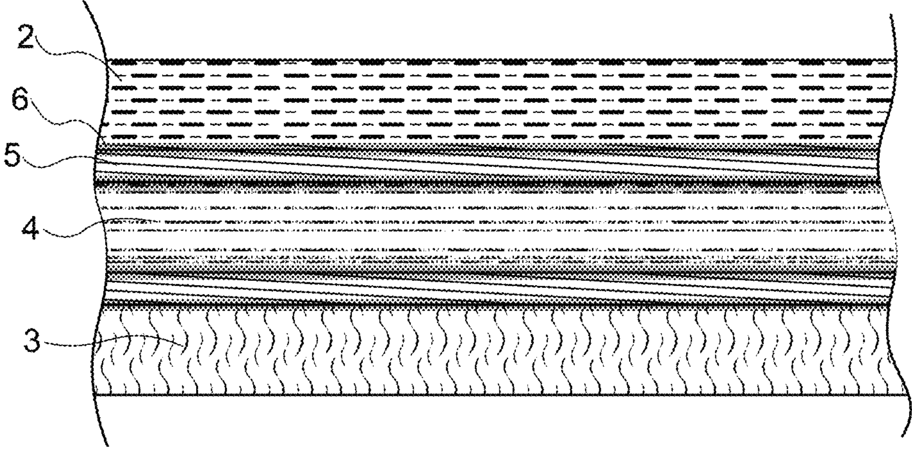
FIG. 4 is a cross-sectional structural schematic diagram of a headgear in accordance with an embodiment.
Figure 5:
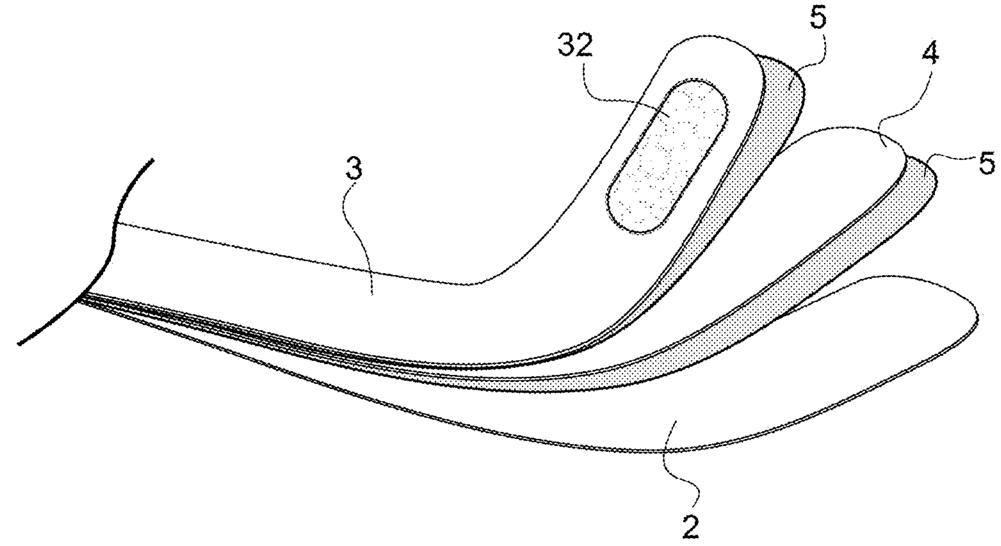
FIG. 5 is a three-dimensional schematic diagram illustrating the layered structure of a headgear in accordance with an embodiment.
Figures 6A, 6B:
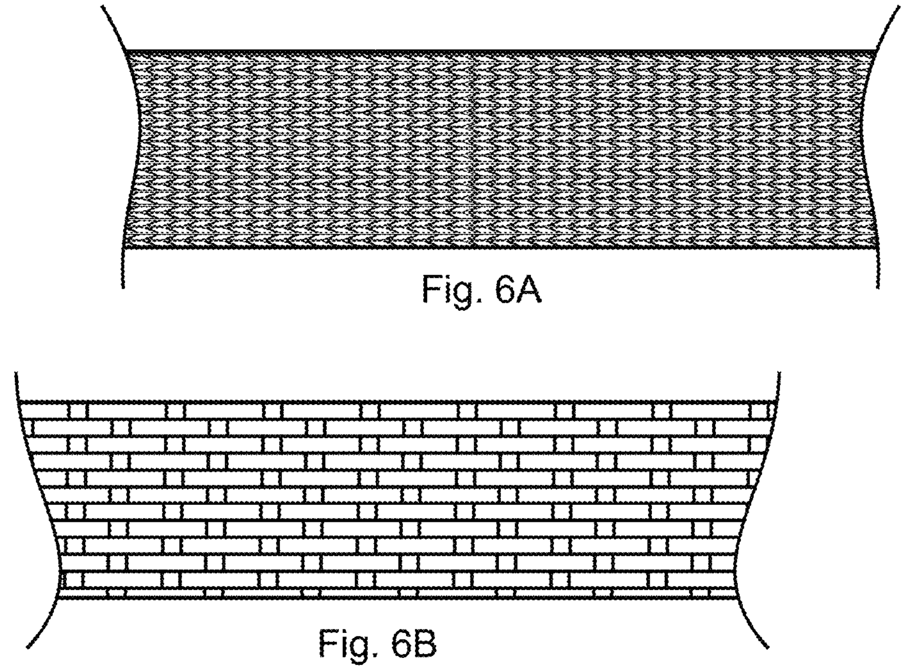
FIGS. 6A and 6B are schematic diagrams showing the weaving method of textile materials of a headgear in accordance with an embodiment.
Figure 7:
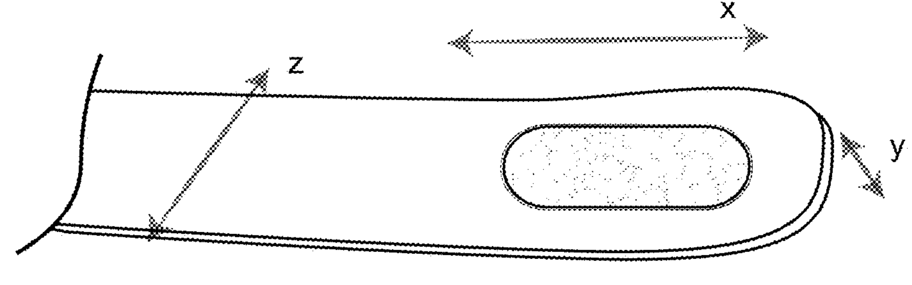
FIG. 7 is a schematic diagram showing the elasticity in various directions of a headgear in accordance with an embodiment.
Figure 7:
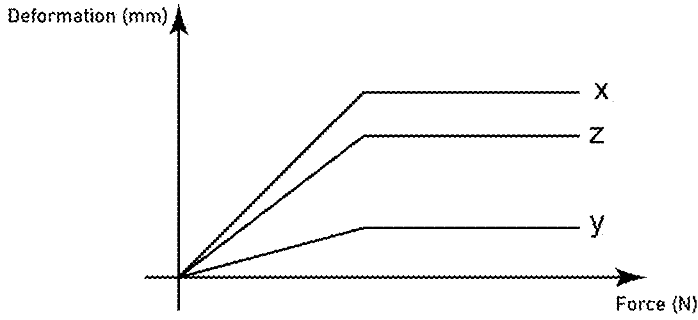
Figure 8:
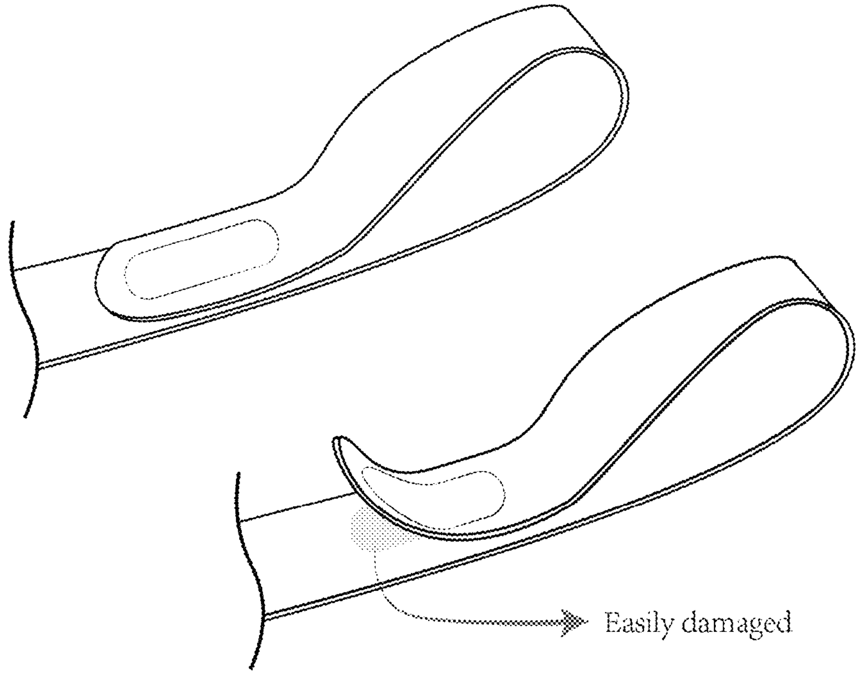
FIG. 8 is a schematic diagram of the connection and tearing between the bonding layer and the fixed part in a headgear in accordance with an embodiment.
Figures 20A, 20B:
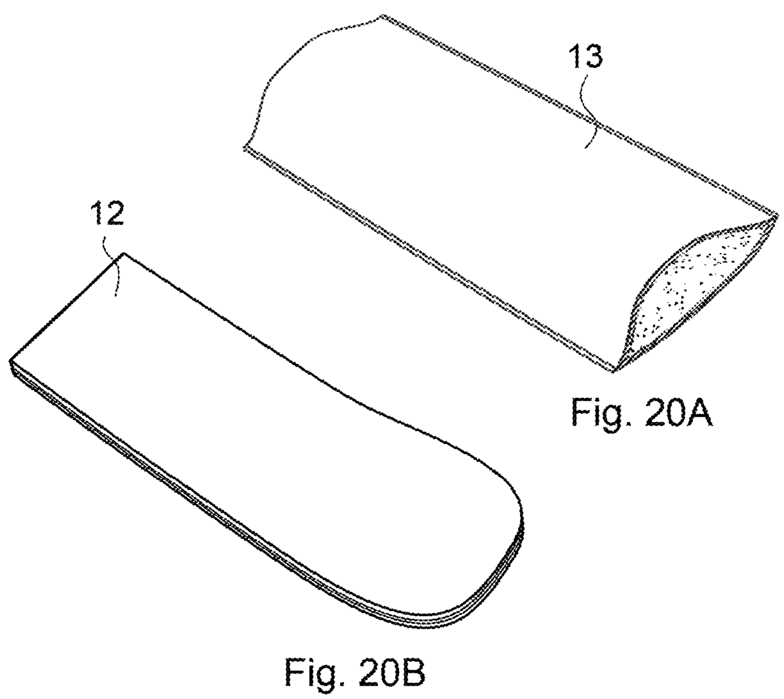
FIGS. 20A and 20B are schematic diagrams displaying a headgear with a reduction of edging or overlocking processes compared to existing headgears with sponge padding in accordance with an embodiment.
Figures 21A, 21B:
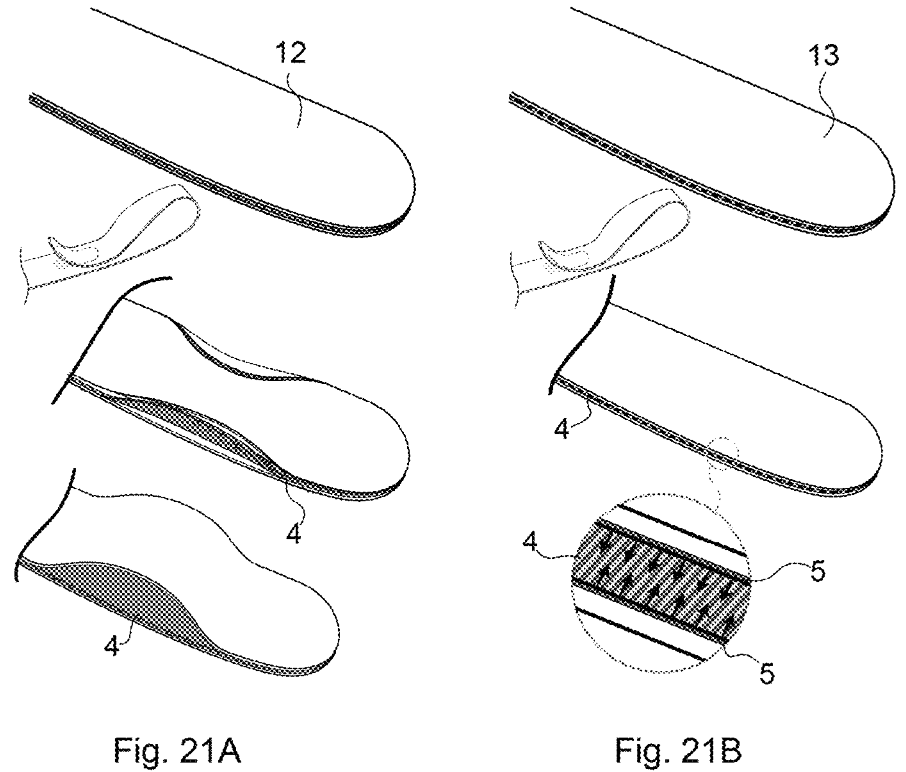
FIGS. 21A and 21B are schematic diagrams illustrating how the headgear is less prone to curling or damage after bonding compared to existing headgears in accordance with an embodiment.

The headgear 1 shown in this disclosure includes five layers and at least two types of textile materials. The various layers of headgear 1 are stacked together and can take multiple different forms (as shown in FIGS. 1 and 2). The inner layer 2, the bonding layer 3, and the padding layer 4 of headgear 1 are equal in size, with their outer edges aligned, while the film layers 5 are equal to or smaller than the inner layer 2, the bonding layer 3, and the padding layer 4. The inner layer 2, the bonding layer 3, and the padding layer 4 are all textile materials. The headgear 1 has at least two types of textile materials and has a certain degree of elasticity in all directions. Since the headgear 1 is folded and bonded along a lengthwise direction of the headgear 1 to adjust its length, the elasticity is maximum along the lengthwise direction of the headgear 1 (as shown in FIG. 7). The textile materials in each layer of the headgear 1 can be of any weaving method (as depicted in FIG. 6), and their colors are also variable. In comparison, the existing market headgears generally includes three layers, with a sponge in the middle and textile materials on either side. The manufacturing process includes material preparation, applying adhesives to the sponge, bonding the sponge with the textile materials, and an additional overlocking step due to easy separation between the sponge and textile materials, followed by stitching (as shown in FIG. 20A). The adhesives used in the processes are ordinary adhesives, which pose certain environmental and health risks. In contrast, the headgear 1 in this disclosure only requires material cutting and stitching (as shown in FIG. 20B), making the process simpler, with lower product and time costs. By using thermoplastic polyurethane and polyurethane reactive adhesives instead of ordinary adhesives, the product is more robust and comfortable to use. The existing headgears with sponge as the padding layer tend to curl at the edges after certain numbers of adhesion and separation with the fixed part, and in severe cases, the bonding layer may separate from other layers, rendering the headgear unusable (as shown in FIG. 21A). However, in this disclosure, the headgear 1 uses thermoplastic polyurethane and polyurethane reactive adhesives for bonding between the layers. After the same number of uses, the film layers 5 and the adhesive 6 will pull the bonding layer 3 inward, preventing the edges from curling or damage (as shown in FIG. 21B). Furthermore, the film layers 5 are made of healthy green materials that are harmless to both human bodies and the environment. Overall, this disclosure improves upon multiple aspects of existing products and is more competitive in the market.

Figure 9:
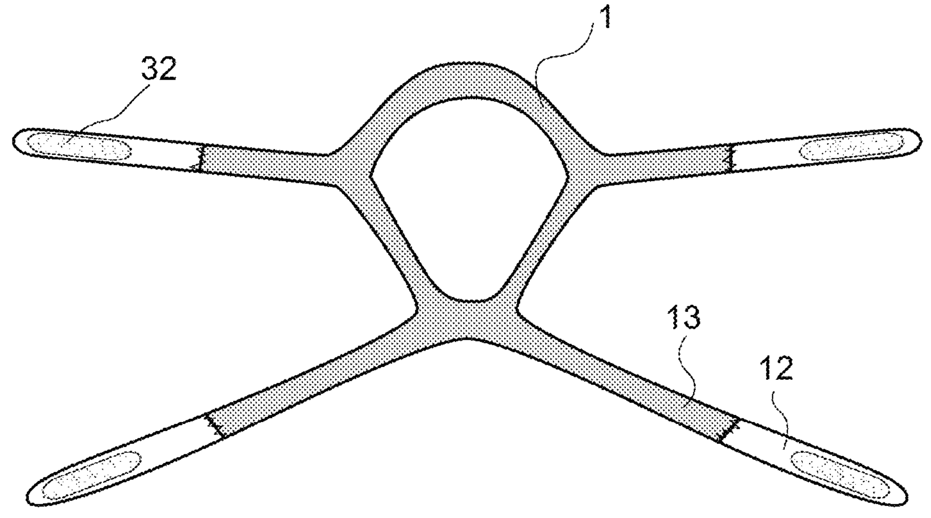
FIG. 9 is a schematic diagram of a composite layer with segmented usage of a headgear in another implementation in accordance with an embodiment.
Figure 10:
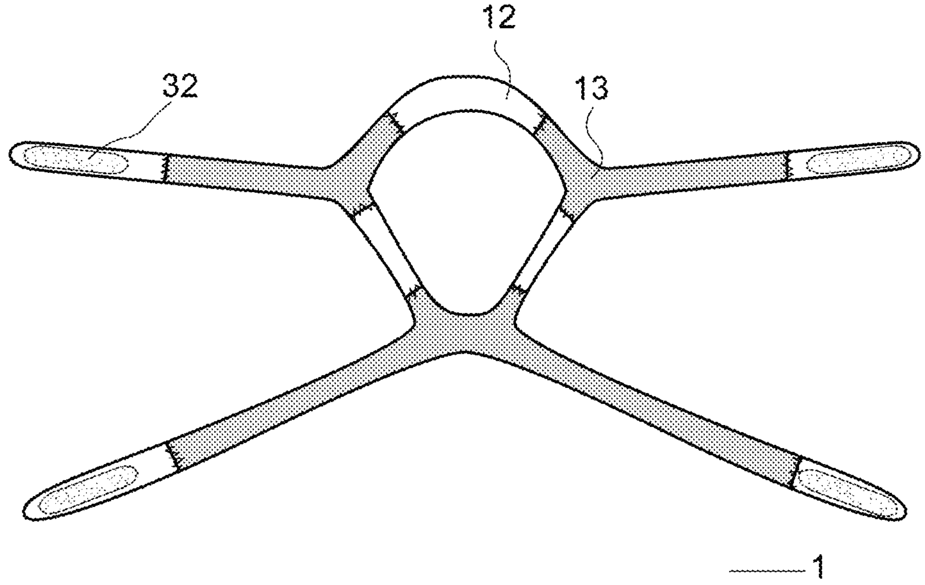
FIG. 10 is a schematic diagram showing another form of a composite layer with segmented usage of a headgear in another implementation in accordance with an embodiment.

In another embodiment, the headgear 1 not only has at least three layers of textile materials disclosed in this disclosure but also includes other existing headgear materials 13, with the layers of the headgear 1 placed in one or more segments (as shown in FIGS. 9 and 10).

In another embodiment, the padding layer 4 uses the same material as the inner layer 2 or the bonding layer 3.

Figure 11:
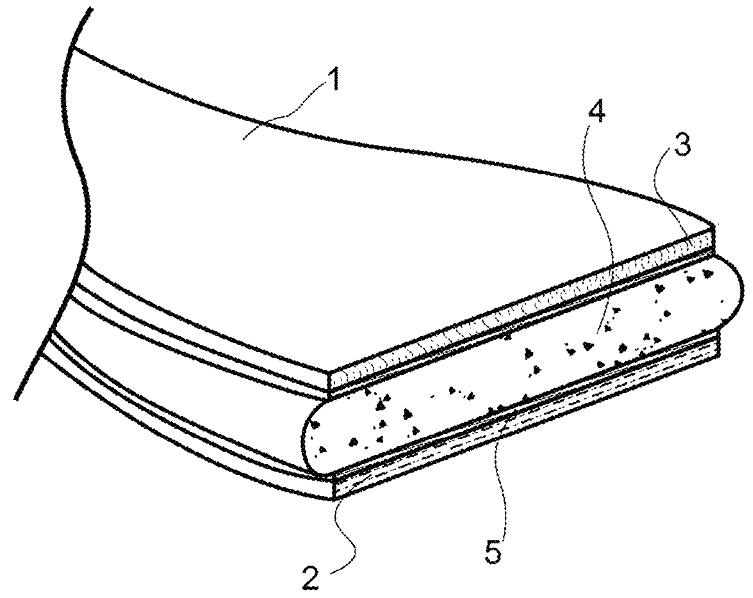
FIG. 11 is a schematic diagram of the padding layer made of foam material in a headgear in another implementation in accordance with an embodiment.

In yet another embodiment, the padding layer 4 of the headgear 1 is made of foam material, not textile material (as shown in FIG. 11).

Figure 12:
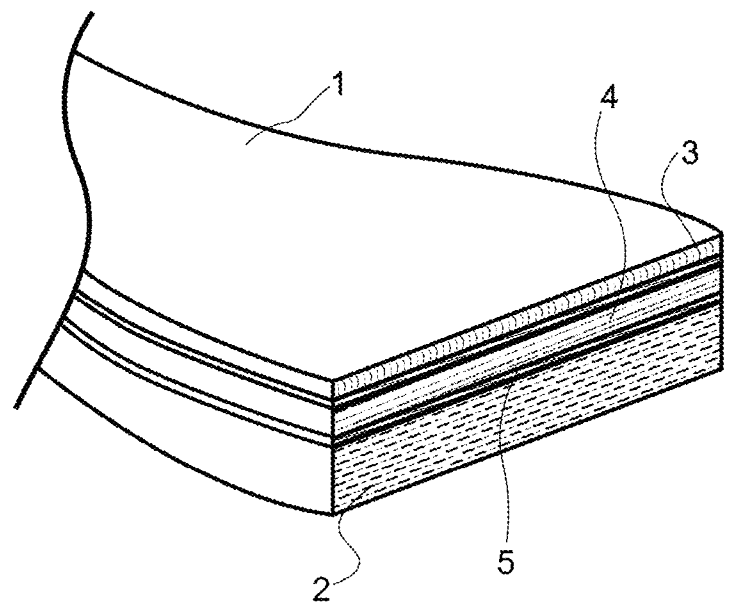
FIG. 12 is a schematic diagram of the inner layer of a headgear being thicker than the padding layer in another implementation in accordance with an embodiment.

In another embodiment, the thickness of the padding layer 4 of the headgear 1 is less than the thickness of the inner layer 2 (as shown in FIG. 12).

Embodiment 2

Figure 13:
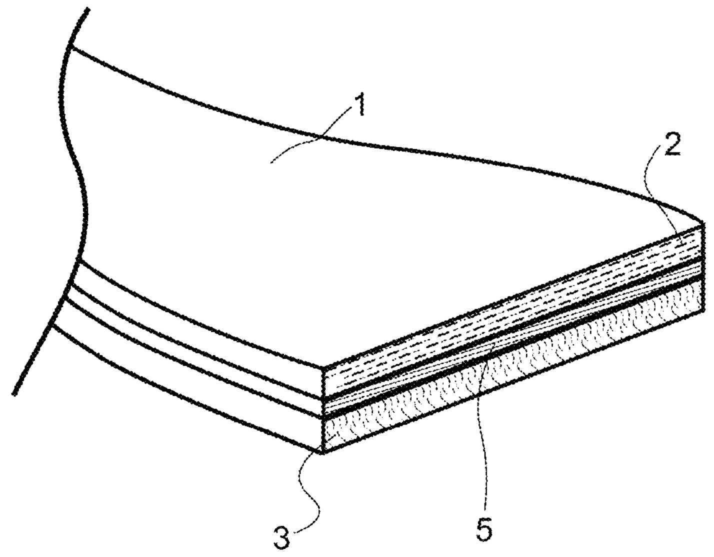
FIG. 13 is a schematic diagram of a headgear without a padding layer in accordance with another embodiment.
Figure 14:
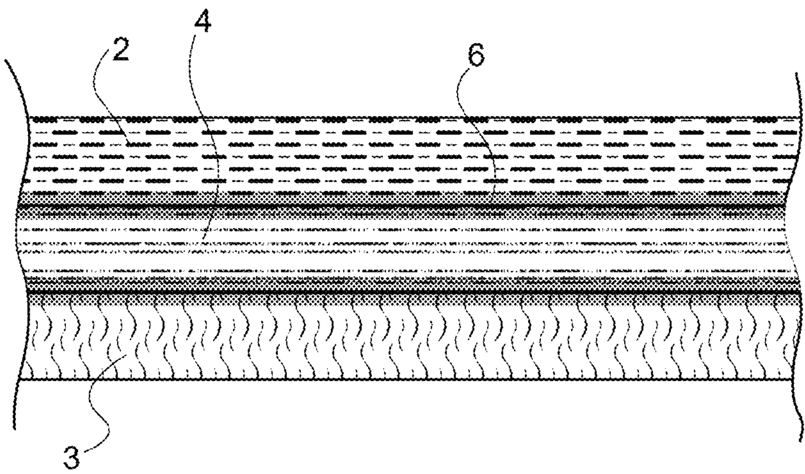
FIG. 14 is a schematic diagram of a headgear without a film layer in another implementation in accordance with another embodiment.

This embodiment provides a headgear 1 for use in the PAP field, as shown in FIGS. 13 and 14. It offers a three-dimensional diagram of the headgear 1. In this embodiment, the difference from the headgear 1 in Embodiment 1 is that the headgear 1 only includes three layers. Compared to the five-layer headgear 1 in Embodiment 1, the three-layer headgear 1 is lighter, reducing the wearing burden for patients. This is advantageous for patients who hope to reduce the weight of the headgear 1. The breathability of the three-layer material is also improved, allowing air to pass through more easily and helping to reduce the feeling of stuffiness or discomfort when the headgear 1 is worn. Besides, the three-layer material reduces production costs since fewer layers mean less material use and shorter manufacturing time, potentially lowering the purchasing cost of the product, making it more competitive among similar products. However, reducing the number of layers also diminishes some of the advantages of the five-layer material. There are two ways to implement the three-layer structure of the headgear 1: one method involves the headgear 1 without a padding layer 4, increasing lightness and breathability (as shown in FIG. 13).

In another embodiment, implementing the three-layer structure of the headgear 1 involves omitting the film layers 5 (as shown in FIG. 14), using adhesive directly for bonding. Although this method loses the environmental benefit of using the film layers 5 and the adhesive 6, the headgear 1 still presents advantages over existing headgears since the headgear 1 uses a combination of textile materials for a stronger, more durable bond, reducing the likelihood of issues like curling and delamination.

Embodiment 3

Figure 15:
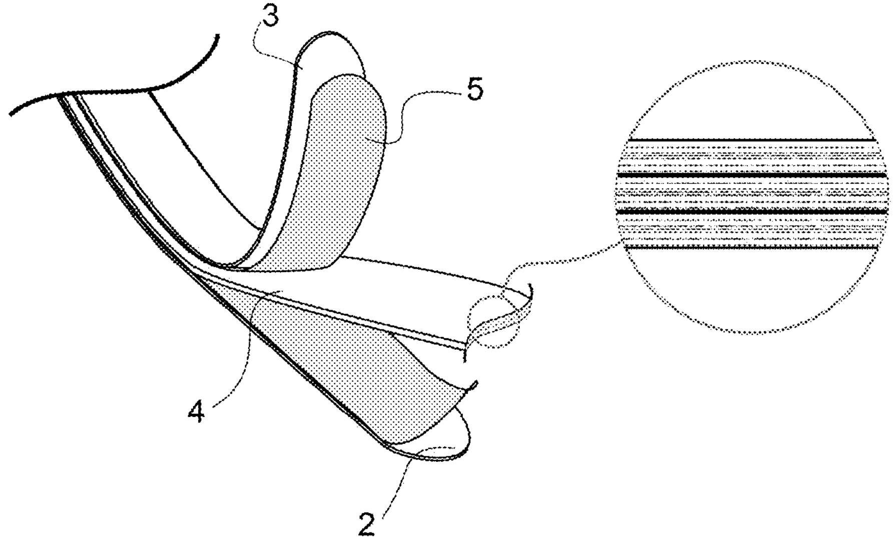
FIG. 15 is a schematic diagram of the padding layer including multiple layers of the same material in a headgear in accordance with an embodiment.
Figure 16:
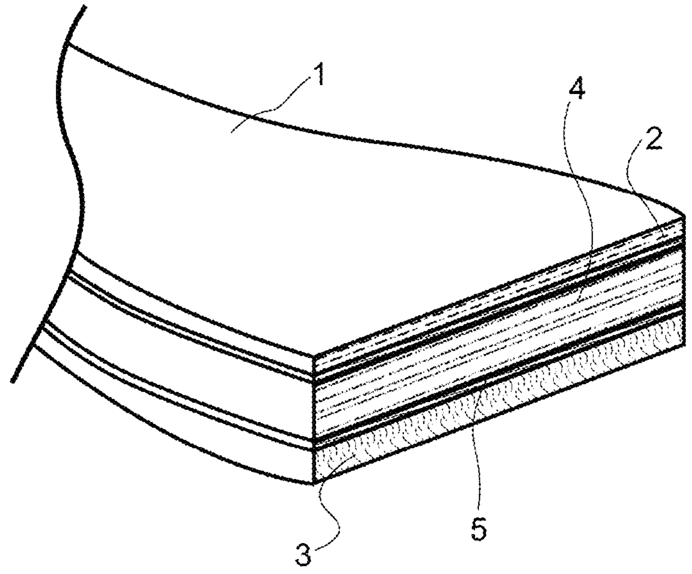
FIG. 16 is a schematic diagram of the padding layer made of a material thicker than the inner layer in another implementation in accordance with an embodiment.
Figure 17:
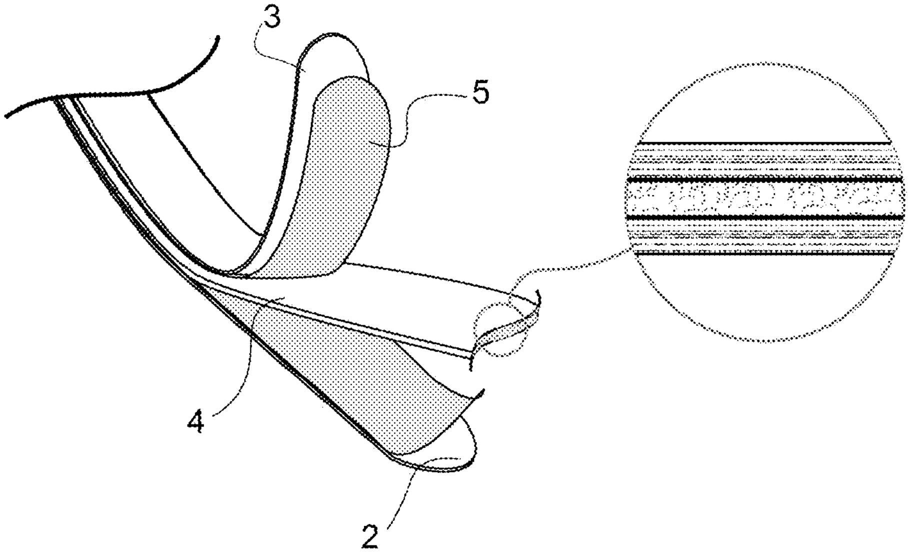
FIG. 17 is a schematic diagram of the padding layer including multiple layers of different materials in a headgear in another implementation in accordance with an embodiment.

This embodiment provides a headgear 1 for use in the PAP field, as shown in FIGS. 15-17. It offers a three-dimensional diagram of the headgear 1. In this embodiment, as illustrated in FIGS. 15-17, the difference from Embodiment 1 is that the padding layer 4 of the headgear 1 is thicker than the inner layer 2. Increasing the thickness of the headgear 1 enhances comfort. Thicker materials provide more cushioning and softness, reducing the pressure of the headgear 1 on the patient's skin. This advantage benefits patients who wear the headgear 1 for extended periods. A thicker padding layer 4 also means that headgear 1 offers better support and stability, helping to ensure that the patient interface cushion is securely positioned on the patient's face without sliding or loosening. Furthermore, a thicker headgear 1 is likely to be more durable, reducing wear or damage from regular use, which means lower repurchase costs for patients. However, any increase in the thickness of the padding layer 4 should not hinder the functionality of the headgear 1. Therefore, a balance between comfort and functionality must be achieved in the design. Specifically, there are three ways to increase the thickness of the padding layer 4: One method involves a headgear 1 with a padding layer 4 including multiple layers of the same material (as shown in FIG. 15).

In another embodiment, the method of increasing the thickness of the padding layer 4 involves a headgear 1 having a padding layer 4 made from a material thicker than the inner layer 2 (as shown in FIG. 16).

In another embodiment, the method of increasing the thickness of the padding layer 4 involves a headgear 1 having a padding layer 4 which includes multiple layers of different materials (as shown in FIG. 17).

Embodiment 4

Figure 18:
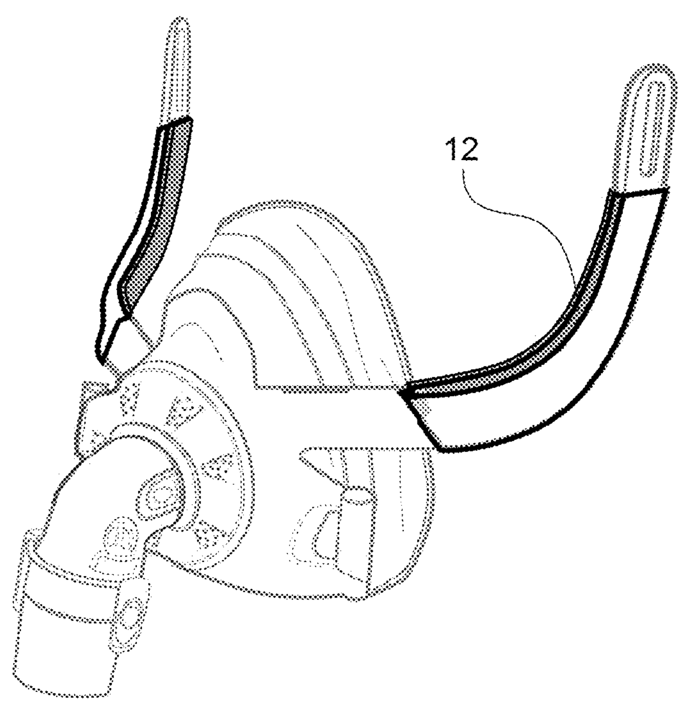
FIG. 18 is a schematic diagram showing at least three layers of textile materials connected to one side of the side straps of the patient interface cushion in accordance with another embodiment.

This embodiment presents a headgear 1 for use in the PAP field, as shown in FIGS. 18 and 19. It offers a three-dimensional diagram of the headgear 1. In this embodiment, the difference from the headgear 1 in Embodiment 1 is that the material combination used in Embodiment 1 is repurposed for a different application: to be used on a frame configured to connect to a patient interface cushion. The material combination used in Embodiment 1, which offers comfort, low production cost, and environmental friendliness, is not only applicable to the headgear 1 but also advantageous in other applications. Using the same materials in different applications can bring cost benefits and simplify inventory management. The materials used for the headgear 1 are applied to a frame (as shown in FIG. 18, the material combination used for the headgear 1 is used for surface bonding with the side straps of the frame). This method realizes different uses for the same material, reducing production costs and streamlining the supply chain, making it an advantageous design method.

Figures 19A, 19B:
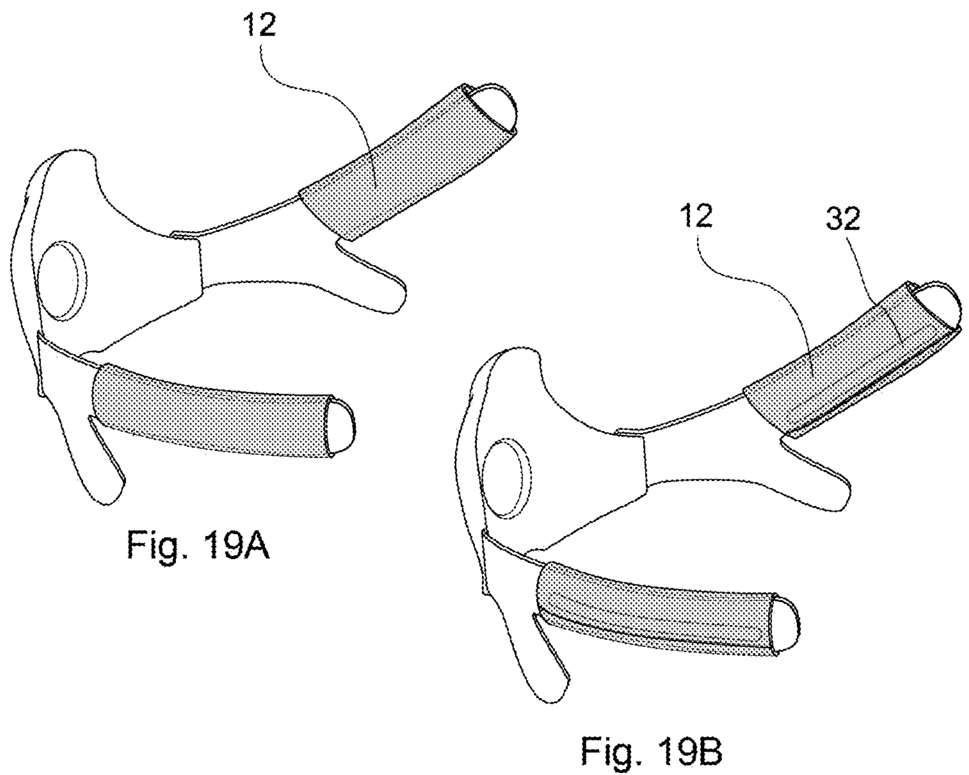
FIGS. 19A and 19B are schematic diagrams showing at least three layers of textile materials configured to surround the side straps of the frame in another implementation in accordance with another embodiment.

In another embodiment, the at least three layers of textile materials disclosed in this disclosure are configured to surround the side straps of the patient interface cushion, which can take two forms. One form is configured to have cylindrical sleeves during manufacturing. During use, the side straps of the patient interface cushion are threaded through one end of the sleeves to the other end, completing the installation (as shown in FIG. 19A). The other form involves at least three layers of textile materials being configured to be secured to a fixed part (like the hook-and-loop fasteners) using adhesive, thermal pressing, or other methods. During use, the textile materials are bonded to the side straps of the frame through the adhesion between the hook-and-loop fasteners and textile materials (as shown in FIG. 19B). This method enhances the comfort of the frame, broadening the range of options for patients. They can choose any frame according to their preferences and needs, and then install the materials disclosed herein onto the side straps to enhance comfort.

The benefits of a headgear provided by this disclosure can at least include:

1) The headgear is more durable and less likely to get damaged with subsequent use, saving patients the cost of repurchasing. Durability is one of the key concerns for patients, especially those with OSA who need to repeatedly put on and adjust the headgear multiple times every night to achieve the right tightness and comfort for their head. This places higher demands on the headgear's durability. a) Headgears currently available on the market often have a sponge layer beneath the bonding layer. However, due to the different material properties of the sponge and textile, they are prone to separation. Additionally, some market headgears with the sponge layer that do not have edging or overlocking tend to fray and delaminate over time. Frequent attaching and detaching of the bonding layer from the fixed part can separate the bonding layer from the sponge, damaging the headgear. Moreover, constant pulling between the bonding layer and the fixed part can also damage the bonding layer itself, rendering it ineffective. The headgear provided in this disclosure does not include a sponge layer. The similar characteristics of the textile materials make bonding between textile materials easier compared to the bonding between sponge and textile. Thus, under the same frequency of attaching and detaching from the fixed part, the headgear made solely of textile materials in this disclosure is more durable than those made of textile and sponge, allowing for longer use by patients with OSA. b) The headgears are generally long-strip in shape and typically exceed 10 cm in length. Long-strip sponge materials, usually made of soft foam or sponge-like polymers, are more susceptible to external forces due to their softness, as opposed to textile materials which are less likely to undergo irreversible shape changes. As a result, textile materials can maintain a relatively flat shape and are less susceptible to curling under external pressure, whereas sponge materials are more prone to bending or curling due to external deformation. Besides, the high deformability of sponge materials means they are more likely to change the shape when subjected to external forces, increasing the risk of curling. Environmental factors such as temperature, humidity, and air pressure can also alter the shape of the sponge, whereas textile materials are more stable. In summary, a headgear formed from the joining of textile materials is less likely to suffer various types of damage and can withstand frequent adjustments (attaching and detaching from the fixed part) without losing performance or structural integrity. Its resistance to damage means that even with frequent fine-tuning by patients, the headgear will maintain its original performance. As the headgear provided in this disclosure has a longer lifespan, patients do not need to purchase replacements frequently, thereby reducing their repurchase costs. As such, the headgear of this disclosure is an economically viable choice for patients and helps to lower the overall cost of treatment.

2) The headgear in this disclosure is relatively simple to manufacture and has lower costs, as well as having fewer processes, which enables rapid market adaptability. The headgears currently available on the market often incorporate a sponge layer sandwiched between textile materials. Due to the difficulty in bonding sponge to textile and the ease of separation under external force, the headgears typically require the sponge to be encased within textile materials and then edge-bonded or overlocked using techniques like thermal pressing or ultrasonic. In contrast, the headgear provided by this disclosure joins textile materials to each other. Since all layers are made of textile materials, they bond more effectively, eliminating the need for edging or overlocking, and ensuring easy adhesion without easy separation. While the existing market process for headgears involves material cutting, compounding, physical overlocking, and stitching, the process for this disclosure is simplified to cutting and stitching, reducing the overlocking step and thereby lowering production costs. This reduction includes savings in labor, equipment, raw materials, and energy, enhancing production efficiency through cost savings. Improved production efficiency means products can be brought to market more quickly and adapt faster to market changes. Moreover, each production step carries a certain risk of errors and defects; reducing the number of steps decreases the likelihood of product defects, thus enhancing quality and reliability.

3) The headgear provided by this disclosure utilizes a film layer of thermoplastic polyurethane and polyurethane reactive adhesives to connect the material layers. This approach is safer and more environmentally friendly compared to existing headgears, which are typically bonded using ordinary adhesives. Additionally, the enhanced durability of the headgear results in a reduced discard rate, further reflecting a green and eco-friendly design. Thermoplastic polyurethane is usually non-volatile and does not release harmful volatile organic compounds, ensuring that its use in bonding does not adversely affect the air quality, thereby contributing to a healthier environment. When it comes to recycling the headgear, thermoplastic polyurethane can be easily separated from other materials for recycling purposes. Some thermoplastic polyurethane materials are biodegradable, which means that they can break down into harmless substances under specific conditions. Certain thermoplastic polyurethane materials can even be recycled for the manufacturing of new products. Polyurethane reactive adhesives, known for their rapid hardening, possess strong adhesive strength and high temperature resistance, outperforming ordinary adhesives in speed of production and durability. And polyurethane reactive adhesives typically exhibit good water resistance, which are suitable for use in humid environments without being susceptible to moisture absorption or detachment. The bonding surface with polyurethane reactive adhesives is very smooth, making the adhesive connection between materials imperceptible to the patient, thus enhancing comfort while also improving the aesthetic appeal of the product. In contrast, ordinary adhesives often contain harmful organic solvents and chemicals, which can pose environmental issues during use and disposal. Using thermoplastic polyurethane and polyurethane reactive adhesives instead of ordinary adhesives is a step towards sustainable development and climate change mitigation and represents an environmentally friendly green design approach. The disclosure aligns with the goal of green design, and due to the durability of the headgear, patients do not need to replace the headgear frequently, thereby reducing the number of discarded products and contributing to a lesser environmental impact, thereby achieving long-term green design goals.

4) Compared to existing headgears on the market, the headgear provided by this disclosure features a more skin-friendly inner layer, a better adhering bonding layer, and the use of anti-static textile materials, all of which contribute to improved quality and comfort. The textile materials used in the skin-contacting inner layer of the headgear in this disclosure are more skin-friendly and softer than those used in the headgears available on the current market. This reduces potential friction and irritation to the skin, lowers the risk of allergic reactions and discomfort for the patient, and helps maintain the skin health of patients. Patients generally prefer products made of skin-friendly materials as they provide better comfort and a more pleasant user experience. Such a design can increase patient satisfaction and trust in the product. Additionally, the bonding layer used for self-folding adhesion in the headgear of this disclosure has better adhesiveness compared to existing products on the market. The headgear is more stable and less likely to fall off when used by patients with OSA, and it does not damage or destroy the surface of the bonding layer when being separated from the fixed part. Therefore, the headgear can be used more durably, allowing for repeated adhering and separating without losing its stickiness. Moreover, the entire headgear is made of antimicrobial materials. Colorfastness is an essential requirement for textile materials to meet wearing standards. Through color change tests on the samples and staining tests on undyed lining textile materials, it has been found that the colorfastness of the headgear in this disclosure is of a higher grade. In addition, the headgear can be made of anti-static textile materials, reducing the likelihood of generating static electricity during use. Therefore, the headgear provided by this disclosure outperforms existing products in terms of quality and comfort.

The embodiments of the disclosure are described above in conjunction with the accompanying drawings, but the disclosure is not limited to the embodiments described above. The specific embodiments are merely illustrative and not restrictive. Those of ordinary skills in this field, in light of the teachings of the disclosure and without departing from the spirit and scope of the disclosure as defined by the claims, can develop numerous forms that fall within the protection of the disclosure.

It must be noted that as used herein and in the appended claims, the singular forms “a”, “an”, and “the” include their plural equivalents, unless the context clearly dictates otherwise.

The invention claimed is:

1. A headgear for use in a Positive Airway Pressure field, configured to secure a patient interface cushion to a face of a patient and to work in conjunction with other components to treat sleep apnea, the headgear comprising:
- an inner layer, a first film layer, a padding layer, a second film layer, and a bonding layer in sequence from a bottom to a top of the headgear,
- wherein the inner layer is configured to be at least partially in contact with a skin of the patient during use;
- wherein the inner layer has at least one of the following features:
- 1) a Grams per Square Meter value of at or between 100 to 450 g/m$^2$;
- 2) material containing 5% to 50% spandex; and
- 3) a thickness of less than 3 mm;
- wherein the bonding layer has a greater roughness than the inner layer, different in a composition or quantity of composition from the inner layer, and configured to adhere an outer side of the headgear that comes into contact with air to a fixed part by folding the headgear to tighten or loosen the headgear;
- an adhesive, configured to bond the layers together;
- wherein the inner layer, the bonding layer, and the padding layer are all textile materials,
- wherein each of the layers has a first end, a second end and a pair of side edges, the pair of side edges defining a width,
- wherein each of the layers has a same width,
- wherein the head gear has a top surface, a bottom surface and a side surface extending between the top surface and the bottom surface, and wherein the pair of side edges of the padding layer are exposed at the side surface, and
- wherein the first film layer and second film layer are polyurethane.

2. The headgear according to claim 1, wherein the padding layer is a combination of multiple layers of textile materials.

3. The headgear according to claim 1, wherein the headgear has an elasticity in all directions, and the elasticity is maximum along a lengthwise direction of the headgear.

4. The headgear according to claim 1, wherein a material of the adhesive includes a combination of one or more of thermoplastic polyurethane, polyurethane reactive adhesives, and other ordinary adhesives.

5. The headgear according to claim 1, wherein the inner layer, the bonding layer, and the padding layer of the headgear are of equal size and their outer edges are aligned with each other.

6. The headgear according to claim 1, the bonding layer and the fixed part are bonded together by thermal pressing.

7. A headgear for use in a Positive Airway Pressure field, configured to secure a patient interface cushion to a face of a patient and to work in conjunction with other components to treat sleep apnea, the headgear comprising:

an inner layer, a first film layer, a padding layer, a second film layer, and a bonding layer in sequence from a bottom to a top of the headgear, wherein the inner layer is configured to be at least partially in contact with a skin of the patient during use;

wherein the bonding layer is different in a composition or quantity of composition from the inner layer and more readily adhesive to a fixed part, and configured to adhere an outer side of the headgear that comes into contact with air to the fixed part by folding the headgear to tighten or loosen the headgear, wherein the bonding layer has at least one of the following features:

1) Including a blend of nylon and spandex;

2) A Grams per Square Meter value of at or between 100 to 450 g/m$^2$; and

3) A thickness of no less than 0.3 mm;

an adhesive, configured to bond the layers together;

wherein the inner layer, the bonding layer, and the padding layer are all textile materials, and the headgear includes at least two types of textile materials, wherein each of the layers has a first end, a second end and a pair of side edges, the pair of side edges defining a width, wherein each of the layers has a same width, and wherein the head gear has a top surface, a bottom surface and a side surface extending between the top surface and the bottom surface, and wherein the pair of side edges of the padding layer are exposed at the side surface, and wherein the first film layer and second film layer are polyurethane.

8. The headgear according to claim 7, wherein the padding layer is a combination of multiple layers of textile materials.

9. The headgear according to claim 7, wherein the inner layer has greater stretchability than the bonding layer.

10. The headgear according to claim 7, wherein a material of the adhesive includes a combination of one or more of thermoplastic polyurethane, polyurethane reactive adhesives, and other ordinary adhesives.

11. The headgear according to claim 7, wherein the padding layer has a composition and quantity of composition different from other layers.

12. The headgear according to claim 7, wherein the bonding layer is rougher than the inner layer.

13. A headgear for use in a Positive Airway Pressure field, configured to secure a patient interface cushion to a face of a patient and to work in conjunction with other components to treat sleep apnea, the headgear comprising:

an inner layer, a first film layer, a padding layer, a second film layer, and a bonding layer in sequence from a bottom to a top of the headgear, wherein the inner layer is configured to be at least partially in contact with a skin of the patient during use;

wherein the bonding layer has a greater roughness than the inner layer, different in a composition or quantity of composition from the inner layer, and configured to adhere an outer side of the headgear that comes into contact with air to a fixed part by folding the headgear to tighten or loosen the headgear;

an adhesive, configured to bond the layers together;

wherein the headgear includes five layers and at least two types of textile materials, wherein each of the layers has a first end, a second end and a pair of side edges, the pair of side edges defining a width, wherein each of the layers has a same width, and wherein the head gear has a top surface, a bottom surface and a side surface extending between the top surface and the bottom surface, and wherein the pair of side edges of the padding layer are exposed at the side surface, and wherein the first film layer and second film layer are polyurethane.

14. The headgear according to claim 13, wherein the padding layer is a single-layer material including foam material or textile material.

15. The headgear according to claim 13, wherein, apart from the adhesive and the film layers, the headgear is made of textile materials.

16. The headgear according to claim 13, wherein a thickness of the padding layer is less than a thickness of the inner layer.

17. The headgear according to claim 13, wherein a material of the film layers is thermoplastic polyurethane.

18. The headgear according to claim 13, wherein a material of the adhesive includes a combination of one or more of thermoplastic polyurethane, polyurethane reactive adhesives, and other ordinary adhesives.

19. A headgear for use in a Positive Airway Pressure field, configured to secure a patient interface cushion to a face of a patient and to work in conjunction with other components to treat sleep apnea, the headgear comprising:

an inner layer, a first film layer, a padding layer, a second film layer, and a bonding layer in sequence from a bottom to a top of the headgear, wherein the inner layer is configured to be at least partially in contact with a skin of the patient during use, wherein the inner layer has at least one of the following features:

1) A Grams per Square Meter value of at or between 100 to 450 g/m$^2$;

2) Material containing 5% to 50% spandex; and

3) A thickness of less than 3 mm;

wherein the bonding layer is different in a composition or quantity of composition from the inner layer, and configured to adhere an outer side of the headgear that comes into contact with air to a fixed part by folding the headgear to tighten or loosen the headgear;

wherein the bonding layer has at least one of the following features:

1) Including a blend of nylon and spandex;

2) A Grams per Square Meter value of at or between 100 to 450 g/m$^2$; and

3) A thickness of no less than 0.3 mm;

wherein the padding layer is configured to be a single-layer material or a multi-layer material;

an adhesive, configured to bond the layers together; and wherein the headgear comprises at least three layers and includes at least two types of textile materials, wherein each of the layers has a first end, a second end and a pair of side edges, the pair of side edges defining a width, wherein each of the layers has a same width, and wherein the head gear has a top surface, a bottom surface and a side surface extending between the top surface and the bottom surface, and wherein the pair of side edges of the padding layer are exposed at the side surface, and wherein the first film layer and second film layer are polyurethane.

20. The headgear according to claim 19, wherein a material of the adhesive includes a combination of one or more of thermoplastic polyurethane, polyurethane reactive adhesives, and other ordinary adhesives.

21. The headgear according to claim 19, wherein the inner layer has greater stretchability than the bonding layer.

22. The headgear according to claim 19, wherein the padding layer is single-layered, the headgear has an elasticity in all directions, and the elasticity is maximum along a lengthwise direction of the headgear.

23. The headgear according to claim 19, wherein the padding layer includes foam material or textile material, and the padding layer includes multiple layers.

24. The headgear according to claim 19, wherein a thickness of the padding layer is greater than the thicknesses of the inner layer and the bonding layer.

* * * * *